Figure 1:
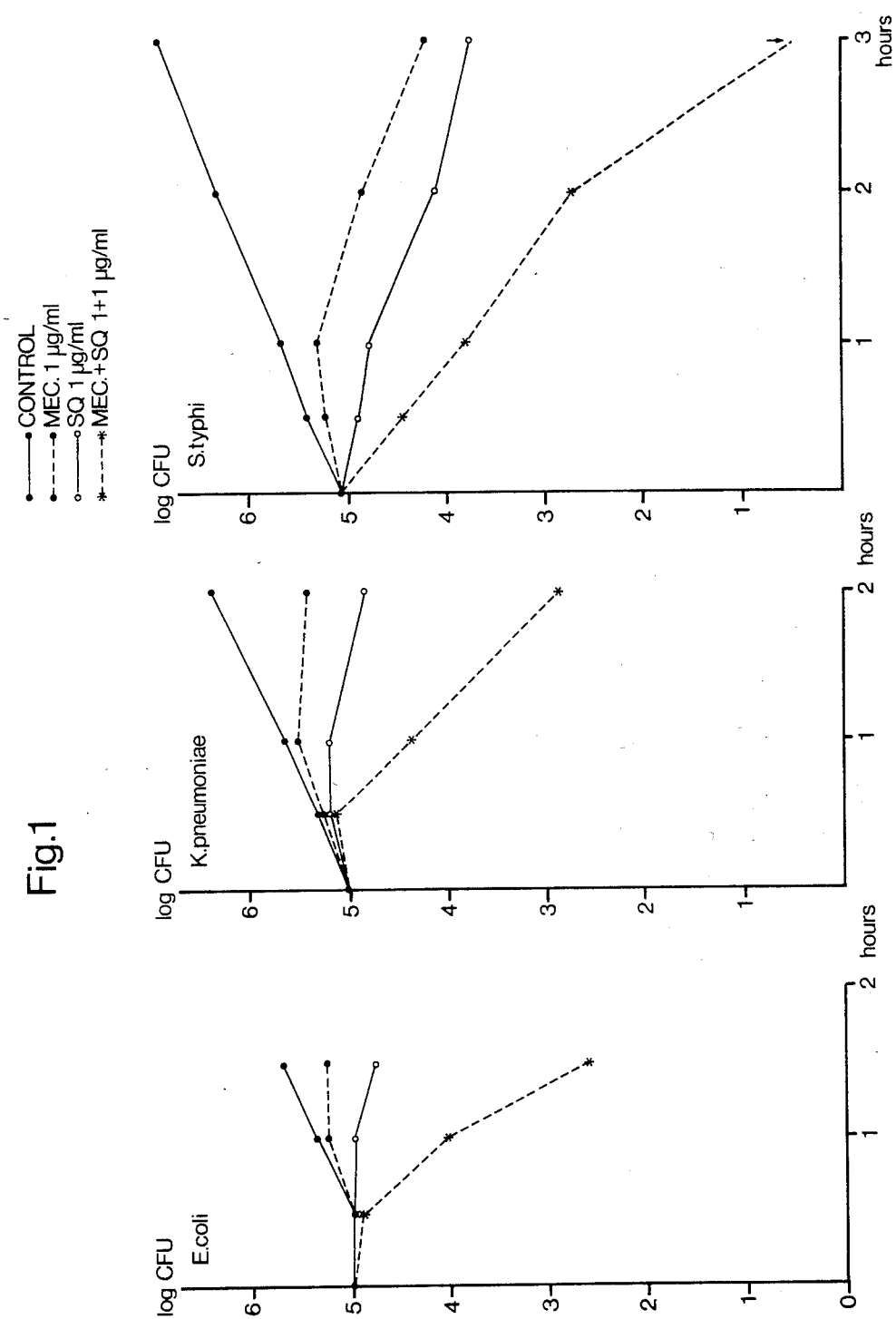

United States Patent [19]

Tybring

[11] Patent Number: 4,557,932
[45] Date of Patent: Dec. 10, 1985

[54] ANTIBACTERIAL SYNERGISTIC PHARMACEUTICAL COMPOSITIONS

[75] Inventor: Leif Tybring, Ølstykke, Denmark

[73] Assignee: Leo Pharmaceutical Products Ltd., Ballerup, Denmark

[21] Appl. No.: 454,491

[22] Filed: Dec. 29, 1982

[30] Foreign Application Priority Data

Feb. 2, 1982 [GB] United Kingdom ............ 8202905

[51] Int. Cl.$^4$ .................. A61K 35/00; A61K 31/43; A61K 31/425
[52] U.S. Cl. ............................. 424/114; 514/365; 514/368
[58] Field of Search .................. 424/270, 271, 114

[56] References Cited

U.S. PATENT DOCUMENTS

3,957,764 5/1976 Lund ............................ 424/270
4,076,816 2/1978 Tybring ........................ 424/271
4,386,034 5/1983 Floyd et al. .................. 260/456 A

FOREIGN PATENT DOCUMENTS

1293590 10/1982 United Kingdom .

OTHER PUBLICATIONS

U.K. Patent Application No. 2071650A, Inventors: Sykes et al., publication date 9-23-1981, (Sykes et al.). Derwent Publication No. 60445 D/34-Belgian Pat. No. 887,428.

Primary Examiner—Jerome D. Goldberg
Assistant Examiner—Joyce L. Morrison
Attorney, Agent, or Firm—Cushman, Darby & Cushman

[57] ABSTRACT

The present invention relates to a new compounded composition with synergistic properties, to dosage units thereof, and to the use of the said compounded composition and dosage units.

The composition contains as active ingredients the amidinopenicillanic acid mecillinam or a pharmaceutically acceptable, non-toxic salt or pro-drug thereof in combination with another antibiotic compound of the formula

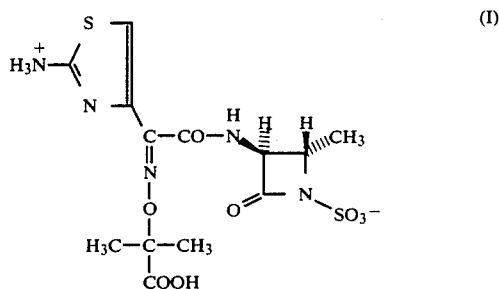

(I)

or a pharmaceutically acceptable, non-toxic salt or pro-drug thereof, optionally together with pharmaceutically acceptable, non-toxic carriers and/or auxiliary agents.

The new composition is valuable in the human and veterinary practice for the treatment of patients suffering from infectious diseases.

9 Claims, 2 Drawing Figures

ANTIBACTERIAL SYNERGISTIC PHARMACEUTICAL COMPOSITIONS

The present invention relates to a new pharmaceutical composition for the treatment of infectious diseases. More particularly, it relates to a compounded composition with synergistic properties, to dosage units thereof, and to the use of the said compounded composition and dosage units in the human and veterinary practice for the treatment of patients suffering from infectious diseases.

The present composition contains as active ingredients the amidinopenicillanic acid mecillinam or a pharmaceutically acceptable, non-toxic salt or pro-drug thereof in combination with another antibiotic compound of the formula

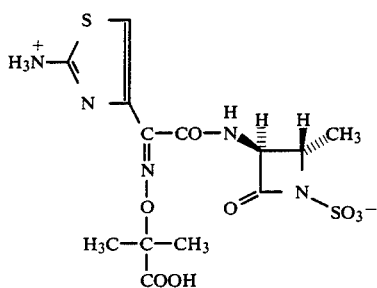

or a pharmaceutically acceptable, non-toxic salt or pro-drug thereof, optionally together with pharmaceutically acceptable, non-toxic carriers and/or auxiliary agents.

The compound of formula I is also known under the code No. SQ 26776.

Both of the active ingredients in the present compositions are known compounds useful in the treatment of patients suffering from bacterial infections. Mecillinam, its salts and pro-drugs thereof are prepared e.g. as described in the specification to British Pat. No. 1,293,590. SQ 26776, its salts and pro-drugs thereof are prepared e.g. as described in the specification to Belgium Pat. No. 887,428.

The expression "pro-drug" as used above and in the following indicates any derivative of mecillinam or the compound SQ 26776 which upon administration to a patient gives rise to the formation of mecillinam or SQ 26776, respectively. When intended for oral use, the said two active ingredients are in particular used in the form of an in the body hydrolyzable ester, including but not limited to alkanoyloxyalkyl and alkoxycarbonyloxyalkyl esters formed with the carboxylic acid group in mecillinam or in SQ 26776. However, esters formed with the sulfo group in SQ 26776, or "soft drugs" of the kind described by Kaminsky and Selk in J. Med. Chem., Volume 23, No. 5 (1980) are equally within the scope of the present invention. The above esters may be used as such or e.g. as salts with a non-toxic, pharmaceutically acceptable acid.

Mecillinam and SQ 26776 may further be included as such in the present compositions, or as salts, such compositions being particularly suited for parenteral use. Suitable salts of the two active ingredients include, but are not limited to sodium, potassium, ammonium, triethylamine, piperidine, morpholine, cyclohexylamine, mono- and diethanolamine, calcium, magnesium, dibenzylethylenediamine, benzyl-β-phenylethylamine, and procaine salts and salts with other antibiotics with acidic or basic characteristics. Mecillinam and SQ 26776 may even form a salt with one another which thus becomes the only active ingredient in the present composition. SQ 26776 is dibasic and may thus form a salt with either one or two cations which may be the same or different. Among the salts preferred, mention may be made of alkali metal salts and salts with other antibiotics with basic characteristics or the salt between the two active ingredients.

Mecillinam may also form salts with pharmaceutically acceptable acids, such as hydrochloric acid, hydrobromic acid, sulfuric acid, phosphoric acid, p-toluenesulfonic acid, naphthalenesulfonic acid, citric acid, maleic acid, etc.

The attainment of a synergistic effect by a combined administration of mecillinam and SQ 26776 is quite unexpected in consideration of the generally accepted circumstances under which such effect will be seen.

From the literature it is known that bacteria when treated with mecillinam are transformed into slowly lysing, big spheric forms (Lund, F. and Tybring, L., Nature New Biology 236 (1972) 135–137; Melchior, N. H., Blom, J., Tybring, L., and Birch-Andersen, A., Acta Pathol. Microbiol. Scand. Sec, B 81 (1973) 393–407). It is further known that bacteria when treated with SQ 26776 are transformed into long, slowly lysing filaments (Data presented at a Symposium on Monobactams at the 12th International Congress of Chemotherapy, Florence 1981). As far as both mecillinam and SQ 26776 are concerned, this characteristic slow lysis takes place within a very broad concentration range.

It has surprisingly now been found that bacteria when treated with the present compositions comprising a mixture of mecillinam and SQ 26776, as such or as salts or pro-drugs thereof, undergo a very quick and drastic lysis. It should be emphasized that this lysis takes place already 10 to 15 minutes after the compositions has been added to the bacterial culture, and further that this very quick and drastic lysis also occurs when the bacterial culture is in its exponential growth phase in a normal growth medium, such as NIH fluid medium, Difco; a quick and drastic lysis as it is obtained with the present compositions has previously only been described when treating bacterial cultures with high concentrations of specific β-lactam antibiotics having particular affinity towards PBP 1a + PBP 1b (PBP = penicillin binding protein) in the cytoplasmic membrane of the bacteria. Therefore it is very surprising that a composition comprising two antibiotics which separately have only a slight affinity towards these PBP's and which separately cause only a slow lysis of the bacteria lead to a very rapid and drastic lysis.

Another advantage of the combined use is a diminished tendency to development of resistant strains of bacteria.

The present compositions can contain further antibiotics which are useful in combatting bacterial infections.

Among suitable β-lactam antibiotics for such compositions can be mentioned: penicillin G and V, ampicillin, amoxycillin, epicillin, carbenicillin, cloxacillin, azlocillin, flucloxacillin, ticarcillin, nafcillin, dicloxacillin, oxacillin, methicillin, carfecillin, cephalothin, cephaloridine, cephaloglycin, cephazolin, cephacetrile, cefoxitin, cephalexin, cephoxazole, cephalonium, or pro-drugs thereof, and mixtures of one or more of such β-lactam antibiotics or pro-drugs thereof, for example: ampicillin/cloxacillin, amoxycillin/cloxacillin, ampicillin/flucloxacillin, amoxycillin/flucloxacillin, and ticarcillin/flucloxacillin, or similar combinations containing pro-drugs, without this enumeration being considered as limiting.

Other antibiotics which can be present in the compositions according to the invention are by way of example: tetracyclines, e.g. tetracycline, oxytetracycline, chlortetracycline, and rolitetracycline; sulphonamides, e.g. sulphadiazine, sulphadoxine, sulphatroxazole, sulphadimidine, sulphathiazole; trimethoprim; aminoglycoside aminocyclitols, e.g. streptomycin, dihydrostreptomycin, kenamycin, gentamycin, neomycin, framycetin, apramycin; aminocyclitols, e.g. spectinomycin; chloramphenicol; fusidic acid; lincomycin; macrolides, e.g. erythromycin, tylosin, spiramycin, oleandomycin; novobiocin; polymyxins, e.g. polymyxin B and E:, and pleuromutilins, e.g. tiamulin, this enumeration not to be considered as limiting the present invention.

The synergistic effect of the present combinations may be utilized either by a reduction in the employed doses whereby the risk of side effects is diminished or may be utilized in combatting less sensitive strains.

The synergistic effect has been observed in a long series of bacteria species, but is especially interesting in species of gram-neg. bacteria, such as *Escherichia coli*, Salmonella, Haemophilus, and Proteus. The in vitro experiments have shown that the ratio of the components in the composition giving rise to the highest degree of synergism depends on both substrate and species.

It should be mentioned, therefore, that in animal experiments or clinical trials, the optimal ratio of the two active components may differ from the ratios of the in vitro experiments, the absorption and excretion rates and the distribution in the body liquids of the active components contained in the composition being factors of importance to the choice of the appropriate ratio between the active ingredients.

In the composition of the invention the ratio of the amidinopenicillanic acid to SQ 26776 goes from 1:100 to 100:1. Within this range the preferred ratio will in most cases be from 1:10 to 10:1, depending on the infection to be combatted and the condition of the patient.

The total amount of active ingredients in the composition lies in the range of from 10 percent to 100 percent of the composition in the case this being in solid form and intended for oral administration and from 0.5 to 30 percent in the case of the composition being in a liquid form intended for injection.

The compositions according to the invention can furthermore contain solid or liquid pharmaceutical carriers and/or auxiliary compounds not interacting with the antibiotic substances, in order to obtain compositions which are usable in particular for enteral, but also for parenteral or topical administration.

Pharmaceutically acceptable, non-toxic organic or inorganic, solid, semisolid, or liquid carriers and/or auxiliary agents suitable for enteral, parenteral or topical administration are e.g. water, gelatine, sugars and sugar alcohols, starches, starch derivatives, cellulose and cellulose derivatives, magnesium or calcium stearate, talc, naturally occurring or modified vegetable and animal fats and oils, mineral oils, benzylalcohol, gums, polyalkylene glycols, polyvinyl derivatives, petroleum jelly, cocoa butter, lanolin, salts for varying the osmotic pressure, buffers, organic acids, carbonates, or other known carriers and/or auxiliary agents for medicaments are all suitable.

The composition produced can either be worked up to pharmaceutical forms of presentation, such as disintegrating, effervescent, or sustained-release tablets, pills, dragees, suppositories or powders, or the composition can be filled into medical containers, such as capsules or ampoules or, as far as suspensions or ointments are concerned, they may be filled into bottles, tubes, or similar containers.

Another object of the invention consists in the selection of a dosage unit which may be advantageously employed in the treatment of infectious diseases.

By the term "dosage unit" is meant a unitary, i.e. a single dose capable of being administered to the patient which may be readily handled and packed, remaining as a physically stable unit dose containing either the active material as such, or the active material mixed with solid or liquid diluents or carriers.

If the composition is to be injected a dosage unit is provided including a sealed ampoule, a vial or a similar container containing a parenterally acceptable, aqueous or oily, injectable solution or dispersion of the active material.

In the treatment of patients suffering from infectious diseases the compositions of the invention are conveniently administered in daily doses from 0.2 g to 5 g of the composition containing the components in an appropriate ratio as mentioned hereinbefore.

Appropriately, the daily dose is given in the form of dosage units, e.g. tablets, of which 1-2 tablets are given 2-4 times a day.

Such dosage units for human use can according to the invention contain from 0.05 g to about 0.5 g in total of a mixture consisting essentially of mecillinam and SQ 26776 or the atoxic salts or pro-drugs thereof, the ratio being from 1:100 to 100:1, preferably from 1:10 to 10:1 of the active components forming the synergistic mixture.

As a non-limiting example can be mentioned a vial containing 100 mg of mecillinam and 100 mg of SQ 26776 as K-salt together with the necessary auxiliary agents for reconstitution in 2-4 ml sterile water for intravenous or intramuscular injection. For adults the dosage may be given 3 to 4 times a day.

It shall be understood, however, that the adequate doses and frequency of administration may vary, depending upon the condition of the patient and the character of the infection, and shall be determined by the medical practitioner.

The dosage unit may also according to the invention be in the form of a dry powdered mixture which immediately before use is suspended in a suitable liquid, e.g. water, soft drinks, milk, or other drinkable liquid. This form of administration is especially useful in the pediatric therapy. The invention comprises also readily usable suspensions of the active compounds in a suitable pharmaceutical vehicle, selected for instance with a view to their stability.

In suspensions is used an ester of mecillinam in the free form or in the form of one of its slightly or sparingly soluble salts, e.g. the hydroiodide, or the p-toluenesulphonate, which examples shall not be limiting for the invention.

The dosage unit of the invention may furthermore contain other components which may contribute to increasing the scope of utility of the composition contained in the dosage unit in question, e.g. other antibiotics as mentioned above, or sulfamylbenzoic acid derivatives which are capable of delaying the excretion of the antibiotics administered.

Furthermore, according to the invention the dosage unit can be in the form of tablets, the inner core of which contains one or more of the active components with the necessary pharmaceutical auxiliary agents, whereas the outer core contains the other active component(s) together with adequate auxiliary agents, or such double tablets are provided in which the halves contain their respective component(s) under conditions where no interaction between the components can occur.

The invention will now be illustrated by the following, non-limiting Examples.

The in vitro activity of mecillinam, SQ 26776 and combinations of the two compounds have been demonstrated in the following Examples.

(A) BACTERICIDAL ACTIVITY

EXAMPLE 1

The bactericidal activity of 1 µg/ml mecillinam, 1 µg/ml SQ 26 776 and the 1+1 µg/ml combination of the two compounds against *Escherichia coli* (Leo HA2) were determined using the plate count method.

An overnight broth culture of the strain was inoculated into a fluid medium, containing:
Yeast extract: 5 g
Casein hydrolysate: 15 g
Dextrose: 1 g
Sodium chloride: 2.5 g
1-Cystine: 0.05 g
Water: 1000 ml
yielding a bacterial concentration of about 100,000 ($10^5$) cells/ml, and the antibiotic solutions in appropriate concentrations were added to the culture. The test tubes were incubated at 37° C.

Samples of the culture were removed at various times, and the number of cells per ml, measured as colony forming units (CFU), was determined using the plate count method. The samples were diluted in fluid medium, mixed with melted agar medium 46° C., containing 100 Leo units β-lactamase per ml and poured into petri dishes.

After overnight incubation at 37° C., the number of colony forming units were counted.

As will appear from FIG. 1, the effect of 1 µg/ml mecillinam on the *E. coli* strain was a decreased growth rate as compared to that of the control culture, followed by a static effect after 1 hour. 1 µg/ml SQ 26776 had a bacteriostatic effect.

The combination of the two compounds resulted in a pronounced bactericidal effect resulting in a 240 fold decrease in CFU compared to the initial cell count.

EXAMPLE 2

Using the technique described in Example 1 and a bacterial culture of *Klebsiella penumoniae* (Leo HE4) incubated at 37° C. for 1 hour before addition of the antibiotics in appropriate concentrations, the antibacterial effect of mecillinam, of SQ 26776, and of a combination of the two compounds were determined.

As will appear from FIG. 1, the effect of 1 µg/ml mecillinam on the *Klebsiella pneumoniae* strain was a decreased growth rate as compared to that of the control culture, followed by a static phase. Under the influence of 1 µg/ml SQ 26776 there was a minor increase of CFU during the first hour, followed by a minor decrease during the second hour.

The combination of 1 µg/ml mecillinam and 1 µg/ml SQ 26776 resulted in a pronounced bactericidal effect resulting in a 160 fold decrease in CFU compared to the initial cell count.

EXAMPLE 3

Using the technique described in Example 2 and a bacterial culture of *Salmonella typhi* (Leo HN), the anti-bacterial effect of mecillinam, of SQ 26776 and of a combination of the two compounds were determined.

As will appear from FIG. 1, the effect of 1 µg/ml mecillinam on the *Salmonella typhi* strain was a decreased growth rate during the first hour as compared to that of the control culture, followed by a slight bactericidal effect, resulting in an 8-fold decrease in CFU compared to the initial cell count.

The effect of 1 µg/ml SQ 26776 was slowly bactericidal, resulting in a 20-fold decrease in CFU.

The combination of 1 µg/ml mecillinam and 1 µg/ml SQ 26776 had an immediate pronounced bactericidal effect, resulting in a decrease of the initial 100,000 ($10^5$) cells/ml to no measurable CFU, i.e. less than 3 CFU/ml.

The results of Examples 1 to 3 have been shown in FIG. 1 in which MEC stands for mecillinam, and SQ stands for SQ 26776.

The bactericidal activity of various concentrations of mecillinam and SQ 26776.

EXAMPLE 4

It has earlier been described that the bactericidal effect of mecillinam is uninfluenced by variations in a broad range of concentrations around 1 µg/ml (Tybring and Melchior, 1975, Antimicrobial Agents and Chemotherapy, 8:271–276).

The bactericidal effect of SQ 26776 against *Klebsiella pneumoniae* (Leo HE4) using the technique described in Example 1 and the concentrations 3 µg/ml, 1 µg/ml, and 0.3 µg/ml was determined.

For the various concentrations tested the bactericidal effect was identical. There was a decreased growth rate as compared to the control culture during the first hour, followed by a minor bactericidal activity resulting in a 6-fold decrease in CFU compared to the initial cell count. These results are in accordance with data presented at a Symposium on Monobactams at the 12th International Congress of Chemotherapy, Florence 1981.

The results of Examples 1 to 4 show that the combined effect of 1 µg/ml mecillinam and 1 µg/ml SQ 26776 is not merely additive, but results in an unexpected, pronounced and early bactericidal activity.

EXAMPLE 5

The antibacterial activity of mecillinam, SQ 26776 and combinations of the two compounds was determined in a biophotometric assay.

Figure 2:
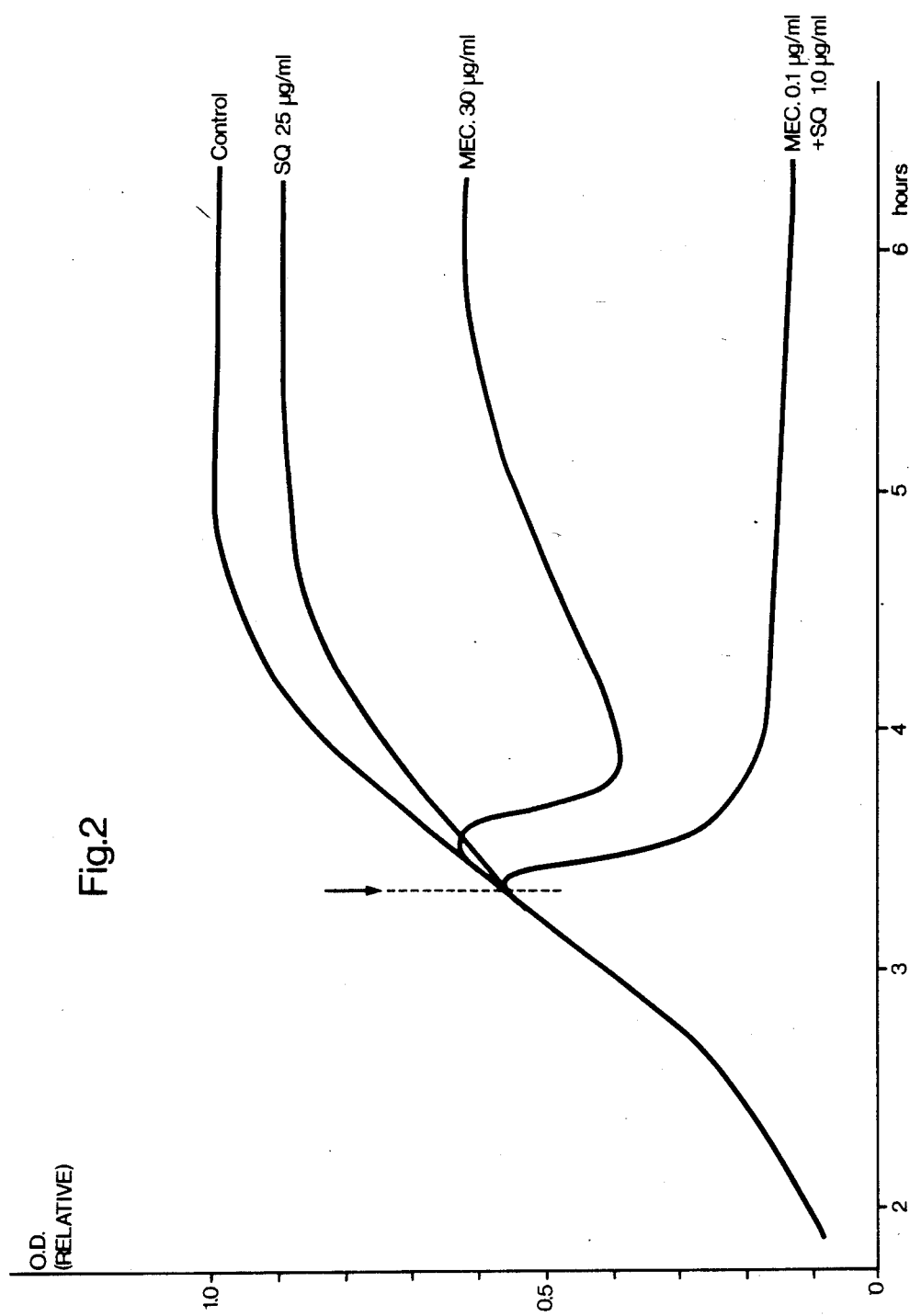

*Escherichia coli* (Leo HA2) was cultured in cuvettes in a biophotometer, and the drugs were added to the cultures in the late log-phase (↓ in FIG. 2). Time-course changes of the turbidity was recorded.

An overnight culture of the strain was inoculated into fluid medium (see Example 1) in the biophotometer and incubated at 37° C. The compounds were added to the cultures in the late log-phase, i.e. 1 hour 30 minutes before the control culture reached the stationary-phase.

The effect of SQ 26776 up to a concentration of 25 µg/ml was a small decrease in bacterial growth as compared to the control culture.

The addition of 30 µg/ml mecillinam resulted in a minor bacteriolytic response after about 10 to 15 minutes. Lower concentrations of mecillinam had less or no effect on the *E. coli* culture.

The combination of the two compounds resulted in an extremely rapid and pronounced bacteriolytic effect after 3 to 5 minutes under the influence of as low as 0.1 µg/ml mecillinam (MEC)+1.0 µg/ml SQ 26776 (SQ).

(B) MORPHOLOGICAL RESPONSE

EXAMPLE 6

An overnight culture of *Escherichia coli* (Leo HA2) was inoculated into fluid medium (see Example 1) and various concentrations of the compounds were added.

For microscopical studies of cell size and form, samples of bacteria were taken at intervals. A loopful was placed on a slide and examined directly under a cover glass, using Nomarski interference contrast (Reichert).

The concentrations used were 10 µg/ml, 1 µg/ml, and 0.1 µg/ml of either mecillinam or SQ 26776, and 10+10 µg/ml, 1+1 µg/ml and 0.1+0.1 µg/ml of the combination of the two compounds.

The morphological response to mecillinam was independent of the concentrations used. After half an hour the originally rod shaped *E. coli* cells were ellipsoidal with pointed ends. After growth for 1 hour under the influence of mecillinam, the cells were ellipsoidal growing to spherical, and after 2 hours the cells were coccoidal to spherical, with about a 4 fold increase in cell volume.

The *E. coli* cells grown under the influence of 10 µg/ml and 1 µg/ml SQ 26776 formed elongated cells after half an hour and grew out to filamentous multinuclear cells 10 to 20 times the length of a control cell, after 1 hour and 2 hours. Under the influence of 0.1 µg/ml SQ 26776 only a minor part of the cells showed morphological changes forming elongated cells after 1 hour and 2 hours.

The combination showed to be very powerful at the concentration 10 µg/ml mecillinam+10 µg/ml SQ 26776 as most of the cells were lysed after half an hour the remaining being ellipsoidal or spindelshaped with damaged cell walls showing bulges of cell mass extruding from the center of the cells. Some of these spindelshaped, strongly damaged cells could be seen in the sample taken after 1 hour. After 2 hours, the cells had lysed, and no cells could be seen under the microscope.

Under the influence of the combination of 1 µg/ml mecillinam and 1 µg/ml SQ 26776 the rod shaped *E. coli* grew to spindelshaped cells during the first half an hour. These cells showed to have a strongly damaged cell wall after 1 hour and after 2 hours the cells had lysed, and no cells could be seen under the microscope.

The combination of 0.1 µg/ml mecillinam and 0.1 µg/ml SQ 26776 gave rise to ellipsoidal cells during the first hour. After 2 hours most of these cells had lysed, and only single coccoidal cell were seen under the microscope.

The experiment showed that mecillinam or SQ 26776 in the concentrations 10 µg/ml, 1 µg/ml and 0.1 µg/ml when used as single compounds influenced the morphology of *E. coli* cells which changed from rodshaped to either ellipsoidal to spheric or elongated to filamentous cells but no cell lysis occured during the first 2 hours.

The combination of the two compounds in the concentrations 10+10 µg/ml, 1+1 µg/ml and 0.1+0.1 µg/ml were strongly active. The rodshaped *E. coli* cells developed spindelshaped cells with damaged cell wall and unexpected cell lysis occurred within 2 hours under the influence of all the concentrations of the combination tested.

The formulation of combinations of mecillinam and SQ 26776 and salts and pro-drugs thereof is illustrated in the following examples.

EXAMPLE 7

| Vial | |
|---|---|
| Mecillinam | 250 g |
| SQ 26776 monopotassium salt | 250 g |
| Sodium acetate anhydrous | 10 g |
| | 510 g |

The components are sieved through a 0.3 mm sieve and blended thoroughly. The powder is dosed into 10 ml vials, each containing 0.51 g of powder mixture. The vials are closed with suitable rubber stoppers.

Each vial is constituted into 4–5 ml of water prior to the use for injection.

EXAMPLE 8

| Tablet | |
|---|---|
| Pivmecillinam hydrochloride | 100 g |
| SQ 26776 amfoion | 400 g |
| Povidone[x] | 3 g |
| Isopropanol | 50 ml |
| Magnesium stearate | 5 g |

[x]Povidone = 1-vinly-2-pyrrolidinone polymers

Pivmecillinam hydrochloride is granulated with a solution of povidone into isopropanol. The granulate is dried on trays at 40° C., sieved through a 0.7 mm sieve and blended with SQ 26776 amfoion and magnesium stearate.

The mixture is compressed to tablets each weighing 0.560 g using a tablet press equipped with circular 12 mm punches and dies.

EXAMPLE 9

| Capsule | |
|---|---|
| Mecillinam | 200 g |
| SQ 26776 amfoion | 200 g |
| Magnesium stearate | 4 g |
| | 404 g |

The substances are sieved through a 0.6 mm sieve and blended. The powder mixture is filled into gelatine capsules size No. 0, each containing 0.404 g of the solid mixture.

EXAMPLE 10

| Intramammmary | |
|---|---|
| Mecillinam | 30 g |
| SQ 26776 monopotassium salt | 30 g |
| Aluminium monostearate | 20 g |
| 12-hydroxystearin[x] | 20 g |

| -continued | |
|---|---|
| Intramammmary | |
| Liquid paraffin | 900 g |

*Trade Mark "THIXCIN ®"

Aluminium monostearate and 12-hydroxystearin are dissolved in liquid paraffin at 130° C. and cooled to 30° C. Mecillinam and SQ 26776 monopotassium salt are milled to a particle size below 50 microns and subsequently dispersed into the intramammary base. After homogenizing using a colloid mill, the intrammary is filled into plastic syringes each containing 5 g of the suspension.

EXAMPLE 11

| Sachet | |
|---|---|
| Pivmecillinam | 100 g |
| SQ 26776 monopotassium salt | 50 g |
| Sucrose | 30,000 g |
| Sodium citrate | 250 g |
| Sodium carboxymethylcellulose | 250 g |
| Peppermint dry flavour | 10 g |

The components are sifted through a sieve 0.5 mm, mixed and filled into unit dose sachets, each containing 3.1 g of powder.

Each powder is constituted into approximately 10 ml of water before use.

What we claim is:

1. An antibacterial synergistic composition consisting essentially of an effective amount of a synergistic mixture of (1) a compound of the formula I

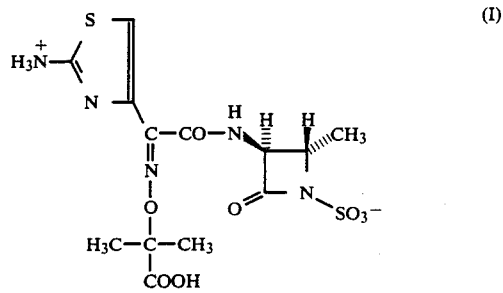

or a pharmaceutically acceptable, non-toxic salt which in oral use is hydrolyzable in the body to give the free acid, and (2) mecillinam or a pharmaceutically acceptable, non-toxic salt which in oral use is hydrolyzable in the body to give mecillinam, the two components (1) and (2) being present in the ratio of 1:10 to 1:1 calculated as the free acids.

2. A synergistic composition according to claim 1 in dosage unit form.

3. A pharmaceutical preparation in dosage unit form for the treatment of patients suffering from infectious diseases caused by bacteria, which comprises as an active ingredient from 0.05 g to about 0.5 g in total of a mixture according to claim 1.

4. The method of treating patients suffering from infectious diseases caused by bacteria which comprises administering by the parenteral route to the patients an effective amount of dosage units as claimed in claim 2.

5. The method of treating patients suffering from infectious diseases caused by bacteria which comprises administering by the enteral route to the patients an effective amount of dosage units as claimed in claim 2.

6. The method of treating patients suffering from infectious diseases caused by bacteria which comprises administering to the patient an effective amount of a synergistic mixture according to claim 1 using a daily dose of from 0.2 g to 5 g in total of said mixture.

7. A method for the treatment of infectious diseases caused by bacteria, comprising simultaneous administration to a host suffering from an infectious disease of a therapeutically acceptable amount of the composition of claim 1.

8. A method for the treatment of infectious diseases caused by bacteria, comprising sequentially administering to a host suffering from an infectious disease a therapeutically acceptable amount of component (1) of claim 1 and a therapeutically acceptable amount of component (2), said components being present in the ratio of 1:10 to 1:1 and acting synergistically in the body fluids.

9. A composition according to claim 1 wherein components (1) and (2) are the compound of Formula I and mecillinam in a ratio of 1:1.

* * * * *